(12) United States Patent
Kellum et al.

(10) Patent No.: US 10,533,989 B2
(45) Date of Patent: Jan. 14, 2020

(54) METABOLOMICS IN PNEUMONIA AND SEPSIS

(71) Applicant: University of Pittsburgh—Of the Commonwealth System of Higher Education, Pittsburgh, PA (US)

(72) Inventors: John A. Kellum, Pittsburgh, PA (US); Christopher W. Seymour, Pittsburgh, PA (US)

(73) Assignee: University Of Pittsburgh—Of The Commonwealth System Of Higher Education, Pittsburgh, PA (US)

( * ) Notice: Subject to any disclaimer, the term of this patent is extended or adjusted under 35 U.S.C. 154(b) by 712 days.

(21) Appl. No.: 14/409,755

(22) PCT Filed: Jun. 25, 2013

(86) PCT No.: PCT/US2013/047662
§ 371 (c)(1),
(2) Date: Dec. 19, 2014

(87) PCT Pub. No.: WO2014/004539
PCT Pub. Date: Jan. 3, 2014

(65) Prior Publication Data
US 2015/0153331 A1 Jun. 4, 2015

Related U.S. Application Data

(60) Provisional application No. 61/664,630, filed on Jun. 26, 2012.

(51) Int. Cl.
*G01N 33/50* (2006.01)
*G01N 33/68* (2006.01)
(Continued)

(52) U.S. Cl.
CPC ..... *G01N 33/5091* (2013.01); *G01N 33/5023* (2013.01); *G01N 33/521* (2013.01);
(Continued)

(58) Field of Classification Search
CPC ............. G01N 33/5091; G01N 33/521; G01N 33/6848; G01N 33/6893; G01N 33/5023; C12Q 2600/118
See application file for complete search history.

(56) References Cited

U.S. PATENT DOCUMENTS

| 2010/0116691 A1* | 5/2010 | Papadimitrakopoulos ............. C12Q 1/002 205/778 |
| 2010/0273207 A1 | 10/2010 | Langley et al. ........... 435/34 |
| 2015/0024969 A1* | 1/2015 | Langley ............. G01N 33/50 506/12 |

FOREIGN PATENT DOCUMENTS

| WO | WO2004/038381 | 5/2004 |
| WO | WO2010/124269 | 10/2010 |

(Continued)

OTHER PUBLICATIONS

Xia et al. (Nucleic Acids Research, 2012, 40:W127-W133).*
(Continued)

*Primary Examiner* — Jeremy C Flinders
(74) *Attorney, Agent, or Firm* — Medlen & Carroll, LLP

(57) ABSTRACT

The present invention describes a global metabolomic profile of patients with community acquired pneumonia (CAP) and sepsis. The metabolomic profile of endogenous small molecules blood was determined using mass-spectrometry. The global metabolomic profile in plasma demonstrated broad differences between CAP and sepsis patients when comparing those who do and do not survive at 90 days. Increases in specific metabolite biomarkers displayed on a heat map provide early diagnosis of these medical condi-
(Continued)

tions to allow for early intervention and aggressive treatment.

18 Claims, 6 Drawing Sheets

(51) Int. Cl.
    G01N 33/52    (2006.01)
    G01N 33/49    (2006.01)

(52) U.S. Cl.
    CPC ..... *G01N 33/6848* (2013.01); *G01N 33/6893* (2013.01); *C12Q 2600/118* (2013.01); *G01N 2570/00* (2013.01); *G01N 2800/12* (2013.01); *G01N 2800/26* (2013.01); *G01N 2800/56* (2013.01); *G01N 2800/60* (2013.01); *G01N 2800/7066* (2013.01)

(56) References Cited

FOREIGN PATENT DOCUMENTS

WO    WO2011/041892    4/2011
WO    WO2013/040099    3/2013

OTHER PUBLICATIONS

Slupsky et al. (Journal of Proteome Research, 2009, 8:5550-5558).*
Laiakis et al. (PLoS ONE, 2010, 5(9):e12655) (Year: 2010).*
Lenz et al. (Journal of Proteome Research, 6:443-458) (Year: 2007).*
Madsen et al. (Analytica Chimica Acta, 659:23-33) (Year: 2010).*
Adams, et al., "The Association of the Kynurenine Pathway of Tryptophan Metabolism with Acute Brain Dysfunction During Critical Illness." *Crit Care Med*, 40(3):835-841 (2012).
Andaluz-Ojeda, et al., "A Combined Score of Pro- and Anti-Inflammatory Interleukins Improves Mortality Prediction in Severe Sepsis." *Cytokine*, 57(3):332-336 (2012).
Beier, et al., "Elevation of Blood Urea Nitrogen Is Predictive of Long-Term Mortality in Critically Ill Patients Independent of "Normal" Creatinine." *Crit Care Med*, 39(2):305-313 (2011).
Bleiblo, et al., "The Role of Immunostimulatory Nucleic Acids in Septic Shock." *Int J Clin Exp Med*, 5(1):1-23 (2012).
Breslow "Maximum Likelihood Estimation of Logistic Regression Parameters under Two Phase, Outcome-Dependent Sampling.". *J R Stat Soc Ser C Appl Stat*, 59:447-461 (1997).
Bruegel, et al., "Sepsis-Associated Changes of the Arachidonic Acid Metabolism and Their Diagnostic Potential in Septic Patients." *Crit Care Med*, 40(5):1478-1486 (2012).
Calvano, et al., "A Network-Based Analysis of Systemic Inflammation in Humans." *Nature*, 437(7061):1032-1037 (2005).
Changsirivathanathamrong, et al., "Tryptophan Metabolism to Kynurenine Is a Potential Novel Contributor to Hypotension in Human Sepsis." *Crit Care Med*, 39(12):2678-2683 (2011).
Chernow, et al., "Hormonal Responses to Graded Surgical Stress." *Arch Intern Med*, 147(7):1273-1278 (1987).
Cohen "The Immunopathogenesis of Sepsis." *Nature*, 420(6917):885-891 (2002).
Darcy, et al., "An Observational Cohort Study of the Kynurenine to Tryptophan Ratio in Sepsis: Association with Impaired Immune and Microvascular Function." *PLoS One*, 6(6):e21185 (2011).
Dehaven, et al., "Organization of Gc/Ms and Lc/Ms Metabolomics Data into Chemical Libraries." *J Cheminform*, 2(1):9 (2010).
Evans, et al., "Integrated, Nontargeted Ultrahigh Performance Liquid Chromatography/Electrospray Ionization Tandem Mass Spectrometry Platform for the Identification and Relative Quantification of the Small-Molecule Complement of Biological Systems." *Anal Chem*, 81(16):6656-6667 (2009).
Ferrer, et al., "Improvement in Process of Care and Outcome after a Multicenter Severe Sepsis Educational Program in Spain." *Jama*, 299(19):2294-2303 (2008).
Gallucci, et al., "Natural Adjuvants: Endogenous Activators of Dendritic Cells." *Nat Med*, 5(11):1249-1255 (1999).
Gough, et al., "The Ratio of Arginine to Dimethylarginines Is Reduced and Predicts Outcomes in Patients with Severe Sepsis." *Crit Care Med*, 39(6):1351-1358 (2011).
Green, et al., "Regulation of Hepatocyte Bile Salt Transporters by Endotoxin and Inflammatory Cytokines in Rodents." *Gastroenterology*, 111(1):193-198 (1996).
Han, et al., "Increased Inos Activity Is Essential for Hepatic Epithelial Tight Junction Dysfunction in Endotoxemic Mice." *Am J Physiol Gastrointest Liver Physiol*, 286(1):G126-136 (2004).
Hasselgren, et al., "Current Concepts of Protein Turnover and Amino Acid Transport in Liver and Skeletal Muscle During Sepsis." *Arch Surg*, 123(8):992-999 (1988).
Hinkelbein, et al., "Alterations in Cerebral Metabolomics and Proteomic Expression During Sepsis." *Curr Neurovasc Res*, 4(4):280-288 (2007).
Ishii, et al., "Genomic DNA Released by Dying Cells Induces the Maturation of Apcs." *J Immunol*, 167(5):2602-2607 (2001).
Izquierdo-García, et al., "A Metabolomic Approach for Diagnosis of Experimental Sepsis." *Intensive Care Medicine*, 37(12):2023-2032 (2011).
Jones, et al., "Lactate Clearance Vs Central Venous Oxygen Saturation as Goals of Early Sepsis Therapy: A Randomized Clinical Trial." *Jama*, 303(8):739-746 (2010).
Kawaguchi, et al., "Cholestasis with Altered Structure and Function of Hepatocyte Tight Junction and Decreased Expression of Canalicular Multispecific Organic Anion Transporter in a Rat Model of Colitis." *Hepatology*, 31(6):1285-1295 (2000).
Kellum, et al., "Understanding the Inflammatory Cytokine Response in Pneumonia and Sepsis: Results of the Genetic and Inflammatory Markers of Sepsis (Genims) Study." *Arch Intern Med*, 167(15):1655-1663 (2007).
Kono and Rock "How Dying Cells Alert the Immune System to Danger." *Nat Rev Immunol*, 8(4):279-289 (2008).
Lagendijk, et al., "The Determination of Allantoin, a Possible Indicator of Oxidant Status, in Human Plasma." *J Chromatogr Sci*, 33(4):186-193 (1995).
Lagu, et al., "Hospitalizations, Costs, and Outcomes of Severe Sepsis in the United States 2003 to 2007." *Crit Care Med*, 40(3):754-761 (2012).
Lawton, et al., "Analysis of the Adult Human Plasma Metabolome." *Pharmacogenomics*, 9(4):383-397 (2008).
Le Gall, et al., "The Logistic Organ Dysfunction System. A New Way to Assess Organ Dysfunction in the Intensive Care Unit. Icu Scoring Group." *Jama*, 276(10):802-810 (1996).
Lee, et al., "Expression of the Bile Salt Export Pump Is Maintained after Chronic Cholestasis in the Rat." *Gastroenterology*, 118(1):163-172 (2000).
Liu, et al., "Metabolomic Analysis of Thermally Injured and/or Septic Rats." *Burns*, 36(7):992-998 (2010).
Marshall, et al., "Multiple Organ Dysfunction Score: A Reliable Descriptor of a Complex Clinical Outcome." *Crit Care Med*, 23(10):1638-1652 (1995).
Matzinger "Tolerance, Danger, and the Extended Family." *Annu Rev Immunol*, 12:991-1045 (1994) A: 991-1020: B: 1021-1045.
Moviat, et al., "Contribution of Various Metabolites to the "Unmeasured" Anions in Critically Ill Patients with Metabolic Acidosis." *Crit Care Med*, 36(3):752-758 (2008).
Ohta, et al., "Untargeted Metabolomic Profiling as an Evaluative Tool of Fenofibrate-Induced Toxicology in Fischer 344 Male Rats." *Toxicol Pathol*, 37(4):521-535 (2009).
Opal "Concept of Piro as a New Conceptual Framework to Understand Sepsis." *Pediatr Crit Care Med*, 6(3 Suppl):S55-60 (2005).
Pan and Raftery "Comparing and Combining Nmr Spectroscopy and Mass Spectrometry in Metabolomics." *Anal Bioanal Chem*, 387(2):525-527 (2007).
Pierrakos and Vincent "Sepsis Biomarkers: A Review." *Critical care*, 14(1):R15 (2010).

(56) References Cited

OTHER PUBLICATIONS

Poeze, et al., "An International Sepsis Survey: A Study of Doctors' Knowledge and Perception About Sepsis." *Crit Care*, 8(6):R409-413 (2004).

Ramazzina, et al., "Completing the Uric Acid Degradation Pathway through Phylogenetic Comparison of Whole Genomes." *Nat Chem Biol*, 2(3):144-148 (2006).

Rivers, et al., "Early Goal-Directed Therapy in the Treatment of Severe Sepsis and Septic Shock." *N Engl J Med*, 345(19):1368-1377 (2001).

Schmerler, et al., "Targeted Metabolomics for Discrimination of Systemic Inflammatory Disorders in Critically Ill Patients." *J Lipid Res*, 53(7):1369-1375 (2012).

Semmler, et al., "Methionine Metabolism in an Animal Model of Sepsis." *Clin Chem Lab Med*, 46(10):1398-1402 (2008).

Serkova, et al., "The Emerging Field of Quantitative Blood Metabolomics for Biomarker Discovery in Critical Illnesses." *Am J Respir Crit Care Med* (2011).

Shapiro, et al., "A Prospective, Multicenter Derivation of a Biomarker Panel to Assess Risk of Organ Dysfunction, Shock, and Death in Emergency Department Patients with Suspected Sepsis." *Crit Care Med*, 37(1):96-104 (2009).

Shi, et al., "Cell Injury Releases Endogenous Adjuvants That Stimulate Cytotoxic T Cell Responses." *Proc Natl Acad Sci U S A*, 97(26):14590-14595 (2000).

Shi, et al., "Molecular Identification of a Danger Signal That Alerts the Immune System to Dying Cells." *Nature*, 425(6957):516-521 (2003).

Sreekumar, et al., "Metabolomic Profiles Delineate Potential Role for Sarcosine in Prostate Cancer Progression." *Nature*, 457(7231):910-914 (2009).

Storey and Tibshirani "Statistical Significance for Genomewide Studies." *Proc Natl Acad Sci U S A*, 100(16):9440-9445 (2003).

Stringer, et al., "Metabolic Consequences of Sepsis-Induced Acute Lung Injury Revealed by Plasma (1)H-Nuclear Magnetic Resonance Quantitative Metabolomics and Computational Analysis." *Am J Physiol Lung Cell Mol Physiol*, 300(1):L4-L11 (2011).

Suhre, et al., "Human Metabolic Individuality in Biomedical and Pharmaceutical Research." *Nature*, 477(7362):54-60 (2011).

Toll, et al., "Validation, Updating and Impact of Clinical Prediction Rules: A Review." *J Clin Epidemiol*, 61(11):1085-1094 (2008).

Trauner, et al., "Endotoxin Downregulates Rat Hepatic Ntcp Gene Expression Via Decreased Activity of Critical Transcription Factors." *J Clin Invest*, 101(10):2092-2100 (1998).

Vincent, et al., "The Sofa (Sepsis-Related Organ Failure Assessment) Score to Describe Organ Dysfunction/Failure. On Behalf of the Working Group on Sepsis-Related Problems of the European Society of Intensive Care Medicine." *Intensive Care Med*, 22(7):707-710 (1996).

Wong, et al., "Genomic Expression Profiling across the Pediatric Systemic Inflammatory Response Syndrome, Sepsis, and Septic Shock Spectrum." *Crit Care Med*, 37(5):1558-1566 (2009).

Wong, et al., "Validation of a Gene Expression-Based Subclassification Strategy for Pediatric Septic Shock." *Crit Care Med*, 39(11):2511-2517 (2011).

Xiao, et al., "A Genomic Storm in Critically Injured Humans." *J Exp Med*, 208(13):2581-2590 (2011).

Xu, et al., "A Metabonomic Approach to Early Prognostic Evaluation of Experimental Sepsis." *J Infect*, 56(6):474-481 (2008).

Zeden, et al., "Excessive Tryptophan Catabolism Along the Kynurenine Pathway Precedes Ongoing Sepsis in Critically Ill Patients." *Anaesth Intensive Care*, 38(2):307-316 (2010).

Rozen, et al., "Metabolomic Analysis and Signatures in Motor Neuron Disease." *Metabolomics*, 1(2):101-108 (2005).

\* cited by examiner

METABOLOMICS IN PNEUMONIA AND SEPSIS

FIELD OF THE INVENTION

This invention is related to global metabolomic profiling in subjects hospitalized with pneumonia and sepsis who died at 90 days compared to survivors. These data revealed physiologically relevant metabolites, consistent with known complex processes in early sepsis (e.g., for example, bile acid metabolism, protein catabolism, inflammation, and/or oxidative stress) that were different in patients versus controls. Moreover, the data demonstrate a potential for metabolomic signatures to uncover novel markers in sepsis, though quantification and validation.

BACKGROUND

Targeted, precise care of patients with sepsis will require a better understanding of mechanisms underlying sepsis and accurate methods to prognosticate sepsis syndromes. Despite decades of work, many sepsis patients go unrecognized by healthcare professionals without receiving recommended treatment. Vincent et al., "The SOFA (Sepsis-related Organ Failure Assessment) score to describe organ dysfunction/failure. On behalf of the Working Group on Sepsis-Related Problems of the European Society of Intensive Care Medicine" Intensive Care Med 1996; 22(7):707-710; Le Gall et al., "The Logistic Organ Dysfunction system. A new way to assess organ dysfunction in the intensive care unit. ICU Scoring Group" JAMA: the journal of the American Medical Association 1996; 276(10):802-810; Marshall et al., "Multiple organ dysfunction score: a reliable descriptor of a complex clinical outcome" Critical Care Medicine 1995; 23(10):1638-1652; Shapiro et al., "A prospective, multicenter derivation of a biomarker panel to assess risk of organ dysfunction, shock, and death in emergency department patients with suspected sepsis" Crit Care Med 2009; 37(1): 96-104; Opal S M., "Concept of PIRO as a new conceptual framework to understand sepsis" Pediatr Crit Care Med 2005; 6(3 Suppl):S55-60; Poeze et al., "An international sepsis survey: a study of doctors' knowledge and perception about sepsis" Crit Care Med. 2004; 8(6):R409-413; and Ferrer et al., "Improvement in process of care and outcome after a multicenter severe sepsis educational program in Spain" JAMA 2008; 299(19):2294-2303. As more patients than ever have sepsis, even small improvements in recognition and tailored treatment may save many lives. Lagu et al., "Hospitalizations, costs, and outcomes of severe sepsis in the United States 2003 to 2007" Critical Care Medicine 2012; 40(3):754-761; Rivers et al., "Early goal-directed therapy in the treatment of severe sepsis and septic shock" N Engl J Med 2001; 345(19):1368-1377; and Jones et al., "Lactate clearance vs central venous oxygen saturation as goals of early sepsis therapy: a randomized clinical trial" JAMA 2010 303(8):739-746.

To this end, hundreds, if not thousands, of diagnostic and prognostic biomarkers are proposed in sepsis. Pierrakos et al., "Sepsis biomarkers: a review" Critical Care Med. 2010; 14(1):R15. These include markers from a variety of biofluids and organs that capture activation of the innate immune response, coagulation cascade, and impaired organ perfusion. Calvano et al., "A network-based analysis of systemic inflammation in humans" Nature 2005; 437(7061):1032-1037; and Cohen J., "The immunopathogenesis of sepsis" Nature 2002; 420(6917):885-891. And yet, few markers successfully guide sepsis treatments, with many notable failures.

To better link new therapies with sepsis mechanisms, the focus of biomarker discovery is increasingly directed towards molecular expression profiles, including gene and protein expression. Wong et al., "Validation of a gene expression-based subclassification strategy for pediatric septic shock" Critical Care Medicine 2011; 39(11):2511-2517; Wong et al., "Genomic expression profiling across the pediatric systemic inflammatory response syndrome, sepsis, and septic shock spectrum" Critical Care Medicine 2009; 37(5):1558-1566; and Xiao et al., "A genomic storm in critically injured humans" J Exp Med 2011; 208(13):2581-2590. Furthest downstream in the biologic system, however, are small metabolites—such as amino acids, carbohydrates, or lipids. These metabolites may offer a more relevant, amplified signature in sepsis and can be measured using techniques such as $^1$H nuclear magnetic resonance (NMR) spectroscopy or mass spectrometry (MS). Serkova et al., "The Emerging Field of Quantitative Blood Metabolomics for Biomarker Discovery in Critical Illnesses" American Journal Of Respiratory And Critical Care Medicine (2011).

To date, the application of metabolomic (or metabonomic) profiling in sepsis is limited to reports on: i) animal studies (Izquierdo-Garcia et al., "A metabolomic approach for diagnosis of experimental sepsis" Intensive Care Medicine (2011); Liu et al., "Metabolomic analysis of thermally injured and/or septic rats" Burns 2010; 36(7):992-998; Hinkelbein et al., "Alterations in cerebral metabolomics and proteomic expression during sepsis" Curr Neurovasc Res 2007; 4(4):280-288; Xu et al., "A metabonomic approach to early prognostic evaluation of experimental sepsis" J Infect 2008; 56(6):474-481; ii) specific metabolic pathways, such as: a) tryptophan/kynurenine (Changsirivathanathamrong et al., "Tryptophan metabolism to kynurenine is a potential novel contributor to hypotension in human sepsis" Critical Care Medicine 2011 39(12):2678-2683; Darcy et al., "An observational cohort study of the kynurenine to tryptophan ratio in sepsis: association with impaired immune and microvascular function" PLoS One 2011 6(6):e21185; Zeden et al., "Excessive tryptophan catabolism along the kynurenine pathway precedes ongoing sepsis in critically ill patients" Anaesthesia And Intensive Care 2010 38(2):307-316; and Adams-Wilson et al., "The association of the kynurenine pathway of tryptophan metabolism with acute brain dysfunction during critical illness"Critical Care Medicine 2012 40(3):835-841); b) arachidonic acid (Bruegel et al., "Sepsis-associated changes of the arachidonic acid metabolism and their diagnostic potential in septic patients" Critical Care Medicine 2012 40(5):1478-1486); c) arginine metabolism (Gough et al., "The ratio of arginine to dimethylarginines is reduced and predicts outcomes in patients with severe sepsis" Critical Care Medicine 2011 39(6):1351-1358); and d) others (Semmler et al., "Methionine metabolism in an animal model of sepsis" Clinical Chemistry And Laboratory Medicine: CCLM/FESCC 2008 46(10):1398-1402; and Moviat et al., "Contribution of various metabolites to the "unmeasured" anions in critically ill patients with metabolic acidosis" Critical Care Medicine 2008 36(3):752-758.

Other preliminary work focuses on $^1$H-NMR metabolomic differences in human, sepsis-associated acute lung injury—where glutathione, adenosine, sphingomyelin, and phosphatidylserine differentiated mechanically ventilated cases from healthy controls. Stringer et al., "Metabolic consequences of sepsis-induced acute lung injury revealed by plasma (1)H-nuclear magnetic resonance quantitative metabolomics and computational analysis" *American Journal Of Physiology Lung Cellular And Molecular Physiology* 2011; 300(1):L4-L11. Yet, it is less clear how the global metabolomic profile is altered in human plasma from subjects with community acquired pneumonia (CAP) or sepsis, nor its potential for mechanism-informed biomarker discovery.

SUMMARY

This invention is related to global metabolomic profiling in subjects hospitalized with pneumonia and sepsis who died at 90 days compared to survivors. These data revealed physiologically relevant metabolites, consistent with known complex processes in early sepsis (e.g., for example, bile acid metabolism, protein catabolism, inflammation, and/or oxidative stress) that were different in patients versus controls. Moreover, the data demonstrate a potential for metabolomic signatures to uncover novel markers in sepsis, though quantification and validation.

In one embodiment, the present invention contemplates a method comprising: a) providing; i) a biological sample derived from a patient suspected of having a medical condition; and iii) a metabolomic platform capable of generating a heat map displaying a pattern comprising a plurality of biomarker metabolites; and b) contacting said sample with said platform under conditions such that said biomarker metabolite pattern diagnoses said medical condition. In one embodiment, the medical condition is diagnosed by the relative abundance of the plurality of biomarker metabolites as compared to a normative population. In one embodiment, the medical condition comprises sepsis. In one embodiment, the medical condition comprises pneumonia. In one embodiment, the pattern of biomarker metabolites is selected from the group consisting of at least one hundred (100) biomarker metabolites, at least two hundred (200) biomarker metabolites, at least three hundred (300) biomarker metabolites, and/or at least four hundred (400) biomarker metabolites. In one embodiment, the plurality of biomarker metabolites comprises bile acid biomarker metabolites. In one embodiment, the plurality of biomarker metabolites comprises oxidative stress biomarker metabolites. In one embodiment, the pattern comprises a damage-associated molecular pattern. In one embodiment, the heat map comprises a plurality of biomarker metabolite regions. In one embodiment, the biomarker metabolite region comprises an amino acid biomarker region. In one embodiment, the biomarker metabolite region comprises a peptide region. In one embodiment, the biomarker metabolite region comprises a carbohydrate region. In one embodiment, the biomarker metabolite region comprises an energy biomarker region. In one embodiment, the biomarker metabolite region comprises a lipid biomarker region. In one embodiment, the biomarker metabolite region comprises a nucleotide biomarker region. In one embodiment, the biomarker metabolite region comprises a cofactor/vitamin biomarker region. In one embodiment, the biomarker metabolite region comprises a xenobiotic biomarker region.

In one embodiment, the present invention contemplates a use of a plurality of biomarker metabolites to manufacture a metabolomic platform capable of generating a heat map for diagnosing a medical condition by identifying a pattern of the plurality of biomarker metabolites from a biological sample derived from a patient suspected of having the medical condition. In one embodiment, the medical condition is diagnosed by the relative abundance of the plurality of biomarker metabolites as compared to a normative population. In one embodiment, the medical condition comprises sepsis. In one embodiment, the medical condition comprises pneumonia. In one embodiment, the pattern of biomarker metabolites is selected from the group consisting of at least one hundred (100) biomarker metabolites, at least two hundred (200) biomarker metabolites, at least three hundred (300) biomarker metabolites, and/or at least four hundred (400) biomarker metabolites. In one embodiment, the plurality of biomarker metabolites comprises bile acid biomarker metabolites. In one embodiment, the plurality of biomarker metabolites comprises oxidative stress biomarker metabolites. In one embodiment, the pattern comprises a damage-associated molecular pattern. In one embodiment, the heat map comprises a plurality of biomarker metabolite regions. In one embodiment, the biomarker metabolite region comprises an amino acid biomarker region. In one embodiment, the biomarker metabolite region comprises a peptide region. In one embodiment, the biomarker metabolite region comprises a carbohydrate region. In one embodiment, the biomarker metabolite region comprises an energy biomarker region. In one embodiment, the biomarker metabolite region comprises a lipid biomarker region. In one embodiment, the biomarker metabolite region comprises a nucleotide biomarker region. In one embodiment, the biomarker metabolite region comprises a cofactor/vitamin biomarker region. In one embodiment, the biomarker metabolite region comprises a xenobiotic biomarker region.

In one embodiment, the present invention contemplates a heat map comprising a metabolomic profile, wherein the heat map comprises a plurality of biomarker metabolite regions, wherein each of the plurality of the biomarker metabolite regions comprise a plurality of biomarker metabolites. In one embodiment, the biomarker metabolite region comprises an amino acid biomarker region. In one embodiment, the biomarker metabolite region comprises a peptide region. In one embodiment, the biomarker metabolite region comprises a carbohydrate region. In one embodiment, the biomarker metabolite region comprises an energy biomarker region. In one embodiment, the biomarker metabolite region comprises a lipid biomarker region. In one embodiment, the biomarker metabolite region comprises a nucleotide biomarker region. In one embodiment, the biomarker metabolite region comprises a cofactor/vitamin biomarker region. In one embodiment, the biomarker metabolite region comprises a xenobiotic biomarker region. In one embodiment, the amino acid biomarker region includes, but is not limited to, an increased N-acetyl serine biomarker, an increased C-glycosyltryptophan biomarker, an increased kynurante biomarker, or an increased urea biomarker as compared to a normative population. In one embodiment, the carbohydrate biomarker region includes, but is not limited to, an increased erythonate biomarker, an increased mannitol biomarker, an increased glycerate biomarker, or an increased xylonate biomarker as compared to a normative population. In one embodiment, the energy biomarker region comprises an increased fumarate biomarker as compared to a normative population. In one embodiment, the lipid biomarker region includes, but is not limited to, an increased glycocholenate sulfate biomarker, an increased taurochenolate sulfate biomarker, an increased 10-heptadecenoate (17:1n7) biomarker, an increased 2-oleoylglycerophospho-ethanolamine biomarker, an increased 1-linoleoyl-glycerophosphoethanolamine biomarker or an increased cortisol biomarker as compared to a normative population. In one embodiment, the nucleotide biomarker region includes, but is not limited to, an increased N1-methyladenosine biomarker, or an increased pseudouridine biomarker as compared to a normative population. In one embodiment, the cofactor/vitamin region includes, but is not limited to, an increased alpha-CHIC glucuronide biomarker, an increased pyridoxate biomarker, or an increased N1-methyl-2-pyridone-5-carboxamide biomarker as compared to a normative population. In one embodiment, the xeobiotic biomarker region includes, but is not limited to an increased paraxanthine biomarker, an increased caffeine biomarker, or an increased erythitol biomarker as compared to a normative population.

Definitions

The term "metabolomic platform" as used herein, refers to any device capable of simultaneous analysis of a biological sample that identifies the type and quantity of biochemicals (e.g., metabolites). The data is may be quantitated and statistically evaluated and/or displayed visually on a heat map.

The term "heat map" as used herein, refers to any graphical representation of data where the individual values contained in a matrix are represented as colors. Fractal maps and tree maps both often use a similar system of color-coding to represent the values taken by a variable in a hierarchy.

The term "biomarker region" as used herein, refers to a specific cluster of biomarkers on a heat map that have a common biochemical function. For example, a heat map may cluster together biomarkers representing amino acid metabolism.

The term "pattern" or "profile" as used herein, refers to the relative abundance of specific biomarker metabolites that is diagnostic of a particular medical condition. Such patterns may be recognized by color coding patterns on a heat map, or by conventional statistical analyses.

The term "biomarker metabolites" as used herein, refers to the final biochemical product of any degradative metabolic pathway that is part of a metabolomic profile (or pattern) that is diagnostic of a particular medical condition.

The term "relative abundance" as used herein, refers to the quantitative difference between at least two biomarker metabolites. Usually, the same biomarker is compared between a patient value and a normative population value. A patient biomarker is said to be "increased" relative to a normative population value if the patient biomarker is found significantly larger in value by using conventional statistical analysis.

The term "normative population value" as used herein, refers to the plasma level of any metabolite that one of skill in the art would expect in a healthy individual. Such nonnative levels are commonly known and published in a wide variety of medical databases, text books and/or practitioner handbooks.

The term "damage-associated molecular pattern", abbreviated DAMP, refers to a biomarker metabolite pattern that is characteristic of cell death (e.g., for example, apoptosis). For example, such DAMP biomarkers reflect the presence of inflammation, oxidation and release biomarker including, but not limited to, intracellular nucleic acid release, uric acid, adenosine or allantoin.

The term "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). For example, a pulmonary sample may be collected by bronchoalveolar lavage (BAL) which comprises fluid and cells derived from lung tissues. A biological sample may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis), cDNA (in solution or bound to a solid support) and the like.

BRIEF DESCRIPTION OF THE FIGURES

FIG. 5A: Stimulation of TNFα in supernatant from differentiated Thp1 monocytes stimulated with PBS (control), ultrapure LPS (1 ng/mL), recombinant human HMGB1 (2 µg/mL), allantoin (0.3 mg/mL), 1-methyladenosine (5 µM), N2-methylguanosine (5 µM), N6-carbamoylthreonyladenosine (5 µM) or betapseudouridine (10 mM) for 16 h.

FIG. 5B: Stimulation of IL1-β level in supernatant from differentiated Thp1 monocytes stimulated with PBS (control), ultrapure LPS (1 ng/mL), recombinant human HMGB1 (2 lg/mL), allantoin (0.3 mg/mL), 1-methyladenosine (5 µM), N2-methylguanosine (5 µM), N6-carbamoylthreonyladenosine (5 µM) or betapseudouridine (10 mM) for 16 h.

FIG. 5C: Stimulation of TNFα in supernatants from differentiated Thp-1 monocytes treated with PBS (control), LPS (4 ng/mL), HMGB1 (5 µg/mL) or beta-pseudouridine (0.0001-10 mM) for 16 h.

FIG. 5D: Stimulation of TNFα level in supernatants from differentiated Thp-1 monocytes treated with PBS (control), LPS (4 ng/mL), HMGB1 (5 µg/mL) or beta-pseudouridine (10 mM) alone or in combination with polymyxin B (PMB; 10 µM) or VIPER (TLR4-antagonist; 10 lµL) for 16 h.

DETAILED DESCRIPTION OF THE INVENTION

Figure 1:
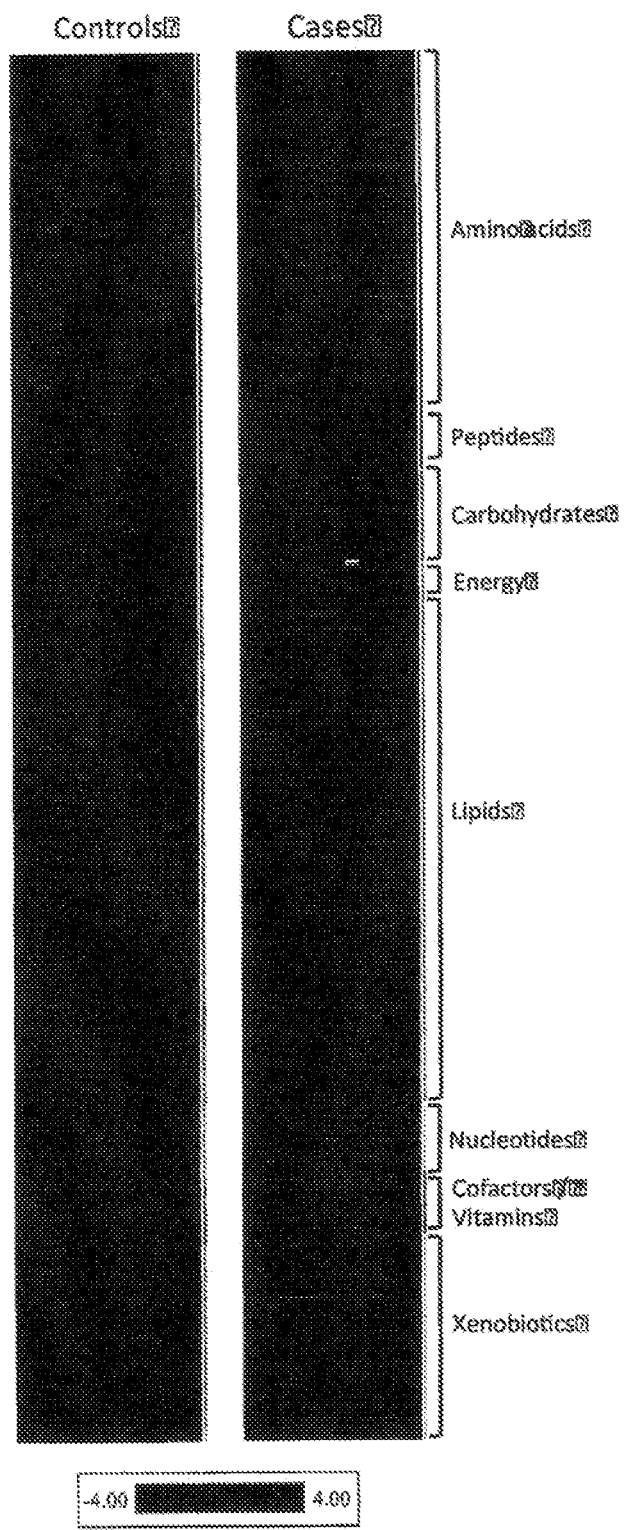
FIG. 1 presents exemplary data showing a heat map representation of an unsupervised hierarchical clustering of 423 identified metabolites. Shades of red or green represent an increase or decrease, respectively, of the metabolite relative to the median metabolite levels of all patients. Controls are subjects who survived at 90 days, and cases are subjects who died on or before 90 days. Metabolites are grouped from top to bottom by metabolic pathways.

This invention is related to global metabolomic profiling in subjects hospitalized with pneumonia and sepsis who died at 90 days compared to survivors. These data revealed physiologically relevant metabolites, consistent with known complex processes in early sepsis (e.g., for example, bile acid metabolism, protein catabolism, inflammation, and/or oxidative stress) that were different in patients versus controls. Moreover, the data demonstrate a potential for metabolomic signatures to uncover novel markers in sepsis, though quantification and validation.

In some embodiment, the present invention contemplates biomarkers (e.g., for example, molecules) that provide diagnostic or prognostic information in patients with suspected sepsis. For example, they may be small molecules having a low molecular weight and identified using mass spectrometry. In preliminary data, these molecules identified patients at higher risk for sepsis and pneumonia than controls. In the future, rapid targeted measurement of these molecules will identify highest risk patients for early treatment. As sepsis has a high mortality rate (~20%), additional prognostic information to recommend aggressive therapy has a potential to save thousands of lives.

In one embodiment, the present invention contemplates biomarkers for sepsis diagnosis and/or prognosis, including, but not limited to, N-acetyl serine, C-glycosyltryptophan, glycocholenate sulfate, taurochenolate sulfate, 10-heptadecenoate (17:1n7), 2-oleoylglycero-phosphoethanolamine, 1-linoleoylglycero-phosphoethanolamine, N1-methyladenosine, pseudouridine, alpha-CEHC glucuronide, N1-methyl-2-pyridone-5-carboxamide, N-acetyl-beta-alanine, S-methylcysteine, N-acetylthreonine, 4-acetamidobutanoate, N-acetylphenylalanine, 1-linoleoylglycerophosphocholine, 2-linoleoylglycerophos-phoethanolamine, 1-arachidonoylglycero-phosphoethanolamine, 5-alpha-pregnan-3alpha,20 beta-diol disulfate 1, N2,N2 dimethylguanosine, N6-carbamoylthreonyl-adenosine and/or allantoin.

One advantage of these biomarkers is an ability to identify downstream effects of gene or protein expression changes as a result of infection and inflammation. Currently available biomarkers in sepsis are rarely low molecular weight (LMW) because of the technological expertise required to measure molecules with mass spectrometry (MS).

The data presented herein evaluates global metabolomic profiles in plasma samples from patients presenting with either CAP and/or sepsis. The subsequent analysis compared the profiles from the patients who did, and did not, survive at 90 days. Patients were randomly selected with extreme differences in sepsis phenotype at presentation, in order to best uncover metabolomic differences. Although it is not necessary to understand the mechanism of an invention, it is believed that differences in plasma metabolites would capture systemic changes across all host organs, particularly in inflammatory, oxidant stress, and energy metabolism pathways. In general, the data was analyzed with classification model building to assess the performance of metabolite-based prognostic models.

The data presented herein demonstrates that biomarker metabolites can serve as classifiers of case/control status determined in at least three ways: 1) random forests, 2) sparse partial least squares regression, and/or 3) ZXY. For example, a random forest model was built using a supervised classification technique based on an ensemble of decision trees (N=50,000). The set of classification trees was based on continual sampling of subjects and biomarker metabolites, and each subject was classified based on the majority votes from all classification trees. In sensitivity analyses, the seed for each model tree was varied and repeated the random forest analysis.

The operating characteristics of these models were summarized using sensitivity, specificity, and the area under the receiver operating characteristic curve (ROC with 95% CI). In this outcome-dependent, stratified study of the GenIMS cohort, the global metabolomic profile of plasma from pneumonia and sepsis subjects at presentation was broadly different when comparing deaths to survivors at 90 days. A mass-spectrometry analysis identified small molecule differences consistent with pathways known to be abnormal in early sepsis. Further, the analysis identified biomarker metabolites, such as modified purine nucleotides, that may be novel markers of oxidative stress and provide putative damage-associated molecular patterns (DAMPs).

The data presented herein validate that small molecules are potential biomarkers of prognosis in sepsis and pneumonia. Broad metabolic differences were found between groups of subjects who did, and did not die, at 90 days, and these changes were in canonical pathways in early pneumonia and sepsis. For example, both primary and sulfated bile acids were elevated in plasma of sepsis deaths, consistent with mechanisms of inflammation-associated cholestasis. These include, but are not limited to, regulation of hepatocyte bile acid transporters at both the basolateral and canalicular membranes, and structural and functional changes to hepatocyte tight junctions. Green et al., "Regulation of hepatocyte bile salt transporters by endotoxin and inflammatory cytokines in rodents" *Gastroenterology* 1996; 111(1):193-198; Trauner et al., "Endotoxin downregulates rat hepatic ntcp gene expression via decreased activity of critical transcription factors" *J Clin Invest* 1998; 101(10):2092-2100; Lee et al., "Expression of the bile salt export pump is maintained after chronic cholestasis in the rat" *Gastroen-* terology 2000; 118(1):163-172: Han et al., "Increased iNOS activity is essential for hepatic epithelial tight junction dysfunction in endotoxemic mice" *Am J Physiol Gastrointest Liver Physiol* 2004; 286(1):G126-136; and Kawaguchi et al., "Cholestasis with altered structure and function of hepatocyte tight junction and decreased expression of canalicular multispecific organic anion transporter in a rat model of colitis" *Hepatology* 2000; 31(6):1285-1295.

The data also demonstrated typical changes in stress response pathways accompanied by increased stimulation of the hypothalamic-pituitary-adrenal axis and elevation of plasma cortisol and corticosterone. Chernow et al., "Hormonal responses to graded surgical stress" *Archives Of Internal Medicine* 1987; 147(7):1273-1278. Changes in protein catabolism were also observed in experimental sepsis. Visceral organs, such as the liver, are believed to increase amino acid uptake to synthesize proteins necessary for the immunologic response to infection, and the present data may identify, in part, an interorgan transfer of amino acids after peripheral release. Hasselgren et al., "Current concepts of protein turnover and amino acid transport in liver and skeletal muscle during sepsis" *Archives Of Surgery* 1988; 123(8):992-999. Finally, allantoin, a marker of oxidative damage, was elevated in sepsis and pneumonia deaths. Lagendijk et al., "The determination of allantoin, a possible indicator of oxidant status, in human plasma" *J Chromatogr Sci* 1995; 33(4):186-193. The enzyme catalyzing the oxidation of uric acid to allantoin is not found in humans, and this metabolite implicates activation of free radical oxidation among cases. Ramazzina et al., "Completing the uric acid degradation pathway through phylogenetic comparison of whole genomes" *Nat Chem Biol* 2006; 2(3):144-148.

Biomarker metabolites may act as DAMPs when released from dying cells. As proposed in one model, the adaptive and innate immune response in sepsis is not just recognition of "non-self" or pathogen molecules, but augmented by "danger" molecules from abnormal host cell death, stress, or injury. Matzinger P., "Tolerance, danger, and the extended family" *Annu Rev Immunol* 1994; 12:991-1045. These non-microbial DAMPs released from cytosol of dying cells then activate both antigen presenting cells and cytotoxic T cells to potentiate the inflammatory cascade. Shi et al., "Cell injury releases endogenous adjuvants that stimulate cytotoxic T cell responses" *Proceedings of the National Academy of Sciences of the United States of America* 2000; 97(26):14590-14595; and Gallucci et al., "Natural adjuvants: endogenous activators of dendritic cells" *Nature Medicine* 1999; 5(11):1249-1255.

DAMPs may include, but are not limited to, intracellular molecules such as uric acid, adenosine metabolites, and double stranded(ds)-DNA having endogenous adjuvant and pro-inflammatory activity. Ishii et al., "Genomic DNA released by dying cells induces the maturation of APCs" *Journal Of Immunology* 2001; 167(5):2602-2607; Shi et al., "Molecular identification of a danger signal that alerts the immune system to dying cells" *Nature* 2003; 425(6957):516-521; and Kono et al., "How dying cells alert the immune system to danger" *Nat Rev Immunol* 2008; 8(4):279-289.

The present data shows that modified purine nucleotides, comprising primarily RNA, were greater in the plasma of sepsis deaths as compared to survivors at 90 days. Unlike in apoptosis, oxidative stress may liberate modified purine nucleotides into the extracellular space like dsDNA, so they no longer remaining hidden to inflammatory effector cells. Bleiblo et al., "The role of immunostimulatory nucleic acids in septic shock" *Int J Clin Exp Med* 2012; 5(1):1-23.

Although it is not necessary to understand the mechanism of an invention it is believed that metabolomics can play a role in biomarker discovery in sepsis. In one embodiment, the present invention contemplates a global metabolomic profile to build prognostic models for 90 days survival, classification of subjects. Although modest, preliminary sensitivity analyses did discriminate between metabolite-only models found in experimental studies of murine sepsis. Many factors, such as sample size, heterogeneity of sepsis course at the time of presentation, and the presence of exogenous metabolites are believed to result in sensitivity differences between clinical datasets as compared to experimental models.

As prognostic performance may differ by choice of biofluid or organ compartment, plasma metabolomics appears to be a preferred analysis platform. Alternative metabolomic prognostic models in sepsis will need a rigorous assessment of their incremental value beyond less costly, more easily measured plasma biomarkers, as well as comparison across organs. Andaluz-Ojeda et al., "A combined score of pro- and anti-inflammatory interleukins improves mortality prediction in severe sepsis" *Cytokine* 2012; 57(3):332-336; and Shapiro et al., "A prospective, multicenter derivation of a biomarker panel to assess risk of organ dysfunction, shock, and death in emergency department patients with suspected sepsis" *Critical Care Medicine* 2009; 37(1):96-104.

The successful application of metabolomics to critically ill patients is uncommon. The inherent variability in metabolic signatures that may occur in critical illness, cost of analyses, and complexity of data limit the routine study of small molecules. However, metabolomic data has offered a functional link to gene and protein expression studies and revealed novel metabolite biomarkers in other conditions. Suhre et al., "Human metabolic individuality in biomedical and pharmaceutical research" *Nature* 2011; 477(7362):54-60; and Sreekumar et al., "Metabolomic profiles delineate potential role for sarcosine in prostate cancer progression" *Nature* 2009; 457(7231):910-914. Metabolomics of sepsis using larger cohort studies comparing different sepsis phenotypes with healthy and non-infected controls, while considering how metabolomics signatures may change over time and in response to treatment.

Mass spectrometry was used to determine relative levels of metabolites between cases and controls but was unable to quantify metabolites in the plasma. Although "targeted", quantitative metabolomics is feasible with $^1$H nuclear magnetic resonance (NMR) spectroscopy but is less sensitive than MS for low concentration molecules. Pan et al., "Comparing and combining NMR spectroscopy and mass spectrometry in metabolomics" *Anal Bioanal Chem* 2007; 387 (2):525-527. For an agnostic exploratory analysis, an inclusive technique was performed. In a larger, independent sample, both novel metabolite pathways in sepsis and performance of metabolite-based prognostic models require confirmation. Toll et al., "Validation, updating and impact of clinical prediction rules: a review" *J Clin Epidemiol* 2008; 61(11):1085-1094. Many confounding factors were unadjusted in the present comparisons. These include the variability in pre-analytic time of samples drawn at presentation or during the administration of treatments (e.g. corticosteroids, supplemental nutrition) for sepsis and/or pneumonia. However, patients were successfully matched on pre-infection characteristics, while selecting extreme phenotypes (both at presentation and 90 days) to uncover broad differences. Finally, a single metabolic signature cannot fully elucidate the mechanisms of small molecule disturbance. For example, a relative increase in urea in cases may result from reduced excretion by the injured kidney, ureagenesis in the liver, protein catabolism, or even exogenous intake. Beier et al., "Elevation of blood urea nitrogen is predictive of long-term mortality in critically ill patients independent of "normal" creatinine" *Critical Care Medicine* 2011; 39(2): 305-313. Targeted metabolomics with relational databases to clinical parameters, protein expression, and putative enzymatic reactions are better suited to understanding the drivers of these complex metabolic pathways.

I. Study Population

Thirty (30) patients were included in an outcome-dependent, stratified random sample, drawn from 1,895 subjects in the original GenIMS study. Pre-illness and matching characteristics, including age, gender, and race, were similar between cases and controls (N=15 each, Table 1).

TABLE 1

Characteristics of cases and controls

| Characteristic | All (N = 30) | Cases (N = 15) | Controls (N = 15) |
|---|---|---|---|
| Matching characteristics | | | |
| Age, y, median [IQR] | 79 [75-82] | 79 [76-82] | 78 [73-83] |
| Male sex, N (%) | 16 (53) | 8 (53) | 8 (53) |
| White race, N (%) | 30 (100) | 15 (100) | 15 (100) |
| Microbiology, N (%) ^ | | | |
| Gram positive | 16 (53) | 9 (60) | 7 (47) |
| Gram negative | 5 (17) | 2 (13) | 3 (20) |
| Procalcitonin > 0.25 mg/ml, N (%) | 17 (57) | 9 (60) | 8 (53) |
| Disease severity and comorbidity | | | |
| Ever smoked, N (%) | 19 (63) | 8 (53) | 11 (73) |
| Charlson co-morbidity index, median [IQR] | 2 [1-3] | 3 [1-4] | 1 [1-2] |
| Charlson greater than zero, N (%) | 26 (87) | 14 (93) | 12 (80) |
| Enrollment PSI, median [IQR] | 107 [76-139] | 125 [105-142] | 82 [0-120] |
| APACHE III score, median [IQR] | 75 [57-80] | 76 [74-95] | 59 [53-75] |
| Enrollment biomarker levels, median [IQR] | | | |
| Interleukin-6, pg/ml | 196 [42-1662] | 433 [196-2663] | 65 [11-443] |
| Interleukin-10, pg/ml | 32.8 [8.6-65.1] | 32.8 [12.3-64] | 43.5 [7.3-216] |
| Tumor necrosis factor, pg/ml | 11.6 [8.8-22.8] | 12.3 [10.2-24.8] | 10.4 [7.8-18.6] |
| Outcomes | | | |
| Antibiotics within 8 hrs of presentation, N (%) | 29 (97) | 15 (100) | 14 (93) |
| Organ failure during hospitalization, N (%) | 28 (93) | 12 (80) | 2 (13) |
| Hospital length of stay, d, median [IQR] | 9 [6-14] | 11 [6-15] | 7 [5-11] |
| Intensive care use, N (%) | 11 (37) | 8 (53) | 3 (20) |
| Mechanical ventilation use, N (%) | 8 (27) | 8 (53) | 0 (0) |

Abbreviations: APACHE III, Acute Physiology and Chronic Health Evaluation III, IQR—interquartile range, PSI—Pneumonia severity
*Comparing cases and controls, using Wilcoxon signed rank test or paired, Students t-test, as appropriate.
^Among patients in whom gram stain of organism was known (N = 21, 70%)

The proportion of patients with greater than one Chanson comorbidity and smoking status (e.g., ever vs. never) were also similar. As expected, subjects who died had greater illness severity measures at presentation, such as pneumonia severity index and APACHE III score (p=0.02). Initial cytokine measurements, including IL-6, IL-10, and tumor necrosis factor were higher in cases, but not significantly different (p=0.15-0.96). Intermediate outcomes such as proportion with organ failure were more common in pneumonia and sepsis deaths than survivors at 90 days (p<0.01).

II. Global Metabolomic Profiles

Figure 2:
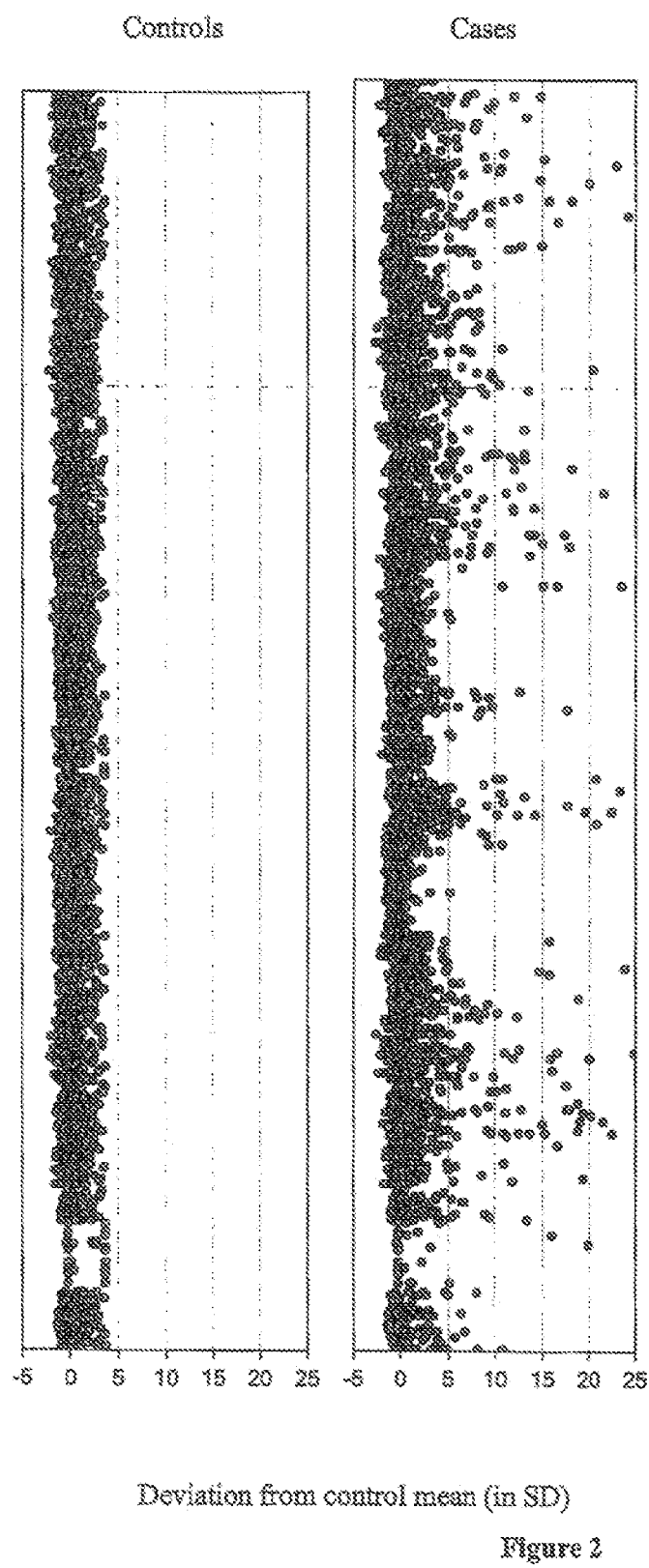
FIG. 2 presents exemplary data showing a Z-score plot for the metabolite data, normalized to the mean of control samples (truncated at 25 standard deviations for clarity). Controls are subjects who survived at 90 days, and cases are subjects who died on or before 90 days. Pathway grouping is similar to FIG. 1.

A global metabolomic profile comparing the patients in Table 1 to population controls provides a measure of metabolite levels scaled to the cohort median value. See, FIG. 1. The differences between patients and controls span a number of processes and metabolic pathways, including, but not limited to, changes in amino acid, nucleotide, energy, bile acid, and sterol metabolism. Four hundred and twenty-three (423) metabolites were identified in plasma samples, of which seventy (70) metabolites were significantly different between patients and controls (p≤0.05). Of these seventy, fifty-six (56) metabolites were below a priori thresholds for false discovery rate (q<0.1). A z-score plot demonstrates the magnitude of metabolite differences in sepsis deaths vs. survivors when normalized area counts were scaled to the control median and standard deviation. See, FIG. 2.

III. Specific Metabolic Pathways

Many metabolites identified in the above global metabolomic profile were significantly different in many notable and complex pathways. See, Table 2 for p<0.01 and Table 3 for p<0.05).

Consistent with cholestasis in sepsis, greater sulfated bile acids (i.e., for example, taurochenolate sulfate, glycochenolate sulfate, p<0.01 for both) and primary bile acids (taurcholate, p<0.05) were observed in patient plasma vs. controls. Differences in steroid metabolism were present, with

TABLE 2

Examples of significant metabolites between non-survivors (cases) and survivors (controls) of pneumonia and sepsis at 90 days. Metabolites selected for illustration if p value ≤ 0.01 and q value < 0.1

| Super pathway | Sub pathway | Metabolite | Relative abundance* | | Exact P value |
|---|---|---|---|---|---|
| | | | Cases | Controls | |
| Amino acids | Serine | N-acetyl serine | 1.23 [1.01-2.32] | 0.79 [0.61, 1.00] | 0.007 |
| | Tryptophan | C-glycosyltryptophan | 1.67 [0.77-2.57] | 0.89 [0.63-1.09] | 0.007 |
| | | kynurenate | 1.30 [0.88-4.29] | 0.64 [0.41-0.97] | 0.007 |
| | Urea cycle | urea | 1.33 [0.97-1.78] | 0.62 [0.53-1.02] | 0.008 |
| Carbo-hydrate | Erythrosugar metabolism | ertyhronate | 1.82 [0.94-3.83] | 0.94 [0.69-1.10] | 0.007 |
| | Mannose metabolism | mannitol | 1.84 [1.00-3.32] | 0.68 [0.25-1.00] | 0.007 |
| | Glycolysis | glycerate | 1.18 [0.95-1.81] | 0.81 [0.57-1.04] | 0.007 |
| | Nucleotide sugar | xylonate | 2.24 [0.85-2.99] | 0.84 [0.64-1.07] | 0.004 |
| Energy | Krebs cycle | fumarate | 1.19 [0.95-1.68] | 0.85 [0.61-1.02] | 0.005 |
| Lipids | Bile acid metabolism | glycocholenate sulfate | 1.64 [1.09-2.09] | 0.79 [0.55-0.95] | 0.001 |
| | | taurochenolate sulfate | 1.72 [1.38-4.48] | 0.60 [0.47-0.88] | <0.001 |
| | Long chain fatty acid | 10-heptadecenoate (17:1n7) | 1.13 [0.92-1.92] | 0.78 [0.52-1.45] | 0.008 |
| | Lysolipid | 2-oleoylglycero-phosphoethanolamine | 0.43 [0.43-0.72] | 1.20 [0.99-1.46] | 0.005 |
| | | 1-linoleoylglycero-phosphoethanolamine | 0.73 [0.46-1.05] | 1.75 [0.93-2.52] | 0.008 |
| | Steroid metabolism | cortisol | 1.55 [0.94-2.35] | 0.50 [0.30-1.08] | 0.004 |
| Nucleotides | Purine/adenosine metabolism | N1-methyladenosine | 1.19 [0.97-1.31] | 0.96 [0.88-1.00] | 0.002 |
| | Pyrimidine metabolism | pseudouridine | 1.32 [0.95-2.26] | 0.87 [0.75-1.07] | 0.003 |
| Cofactors/vitamins | Tocopherol metabolism | alpha-CEHC glucuronide | 0.82 [0.40-2.85] | 0.36 [0.36-0.82] | 0.002 |
| | Vitamin B6 | pyridoxate | 3.96 [1.07-10.96] | 0.63 [0.49-0.96] | <0.001 |
| | Nicotinate and nicotinamide metabolism | N1-methyl-2-pyridone-5-carboxamide | 1.98 [0.99-3.67] | 0.71 [0.53-1.02] | 0.008 |
| Xenobiotics | Xanthine metabolism | paraxanthine | 0.35 [0.14-0.90] | 1.17 [0.68-1.67] | 0.004 |
| | | caffeine | 0.34 [0.15-1.09] | 1.14 [0.69-2.24] | 0.010 |
| | Sugar substitute | erythritol | 1.71 [0.96-3.20] | 0.87 [0.62-1.08] | 0.008 |

*Relative abundance determined as median [IQR] of normalized, imputed raw area counts
^P values determined using the Wilcoxon signed rank test

TABLE 3

Examples of significant metabolites between non-survivors (cases) and survivors (controls) of pneumonia and sepsis at 90 days. Metabolites shown if p value ≤ 0.05 and q value < 0.1.

| Super pathway | Sub pathway | Metabolite |
|---|---|---|
| Amino acids | Alanine | N-acetyl-beta-alanine |
| | Cysteine | S-methylcysteine |
| | Threonine | N-acetylthreonine |
| | Guanidino and acetamido | 4-acetamidobutanoate |
| | Phenylalanine | N-acetylphenylalanine |
| Carbo-hydrate | Erythrosugar metabolism | ertyhronate |
| | Sucrose metabolism | sucrose |
| | Glycolysis | glycerate |
| | Nucleotide sugar | arabitol |
| | | threitol |
| Lipids | Fatty acid, dicarboxylate | hexadecanedioate |
| | Lysolipid | 1-linoleoylglycerophos-phocholine |
| | | 2-linoleoylglycerophos-phoethanolamine* |
| | | 1-arachidonoylglycero-phosphoethanolamine* |
| | Steroid metabolism | 5alpha-pregnan-3alpha, 20 beta-diol disulfate 1* |
| Nucleotides | Purine/adenosine metabolism | N2, N2 dimethylguanosine |
| | | N6-carbamoylthreonyl-adenosine |
| | | allantoin |

Metabolites selected for illustration if p value ≤ 0.05 and q value < 0.1
*Relative abundance determined as median [IQR] of normalized, imputed raw area counts
^P values determined using the Wilcoxon signed rank test significantly greater cortisol (p<0.01), cortisone (p<0.05), and sulfated hormones suggestive of increased storage (i.e., for example, 5-alpha-pregnan-3alpha, 20-beta-diol disulfate, 21-hydroxypregnenolone disulfate, pregnenolone sulfate, and prenanediol-3-glucuronide, p<0.04 for all).

Figure 3:
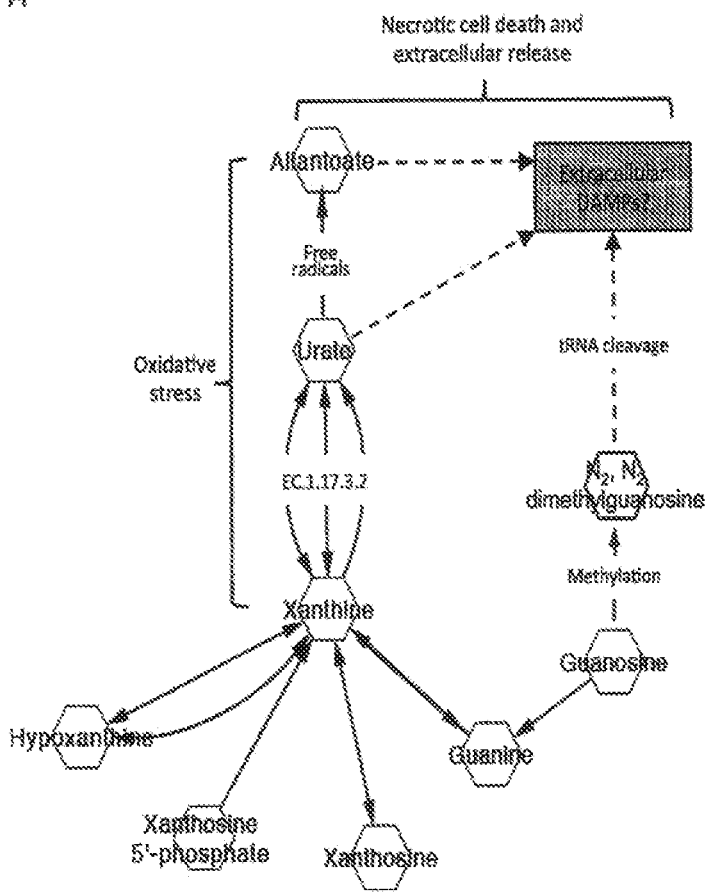
FIG. 3 presents an illustrative schematic of purine pathways using the Cytoscape platform (cytoscape.org) with Metscape plugin. Hexagons represent metabolite compounds, with pathways simplified for illustration (panel A). Oxidative stress due to sepsis and pneumonia potentiates oxidation of xanthine to uric acid by xanthine oxidase (EC.1.17.3.2). Oxygen free radicals also oxidize urate/uric acid to allantoin/allantoate. In the current work, the relative amount of allantoin (panel B, $p<0.01$) was greater in cases than controls. Urate levels were no different between groups (panel C, $p=0.35$). Oxidative stress may also induce RNA cleavage, releasing modified purine nucleosides in the cytoplasm. We observed greater relative levels of plasma $N_2$, $N_2$-dimethylguanosine (panel D, $p<0.01$, $q<0.1$), N6-carbamoylthreonyladenosine ($p<0.05$, $q<0.1$, not shown), and N1-methyladenosine ($p<0.05$, $q<0.1$, not shown) in cases vs. controls. After necrotic cell death, these nucleotide metabolites may further the inflammatory cascade by acting as damage-associated molecular patterns (DAMPs).
Figure 3:
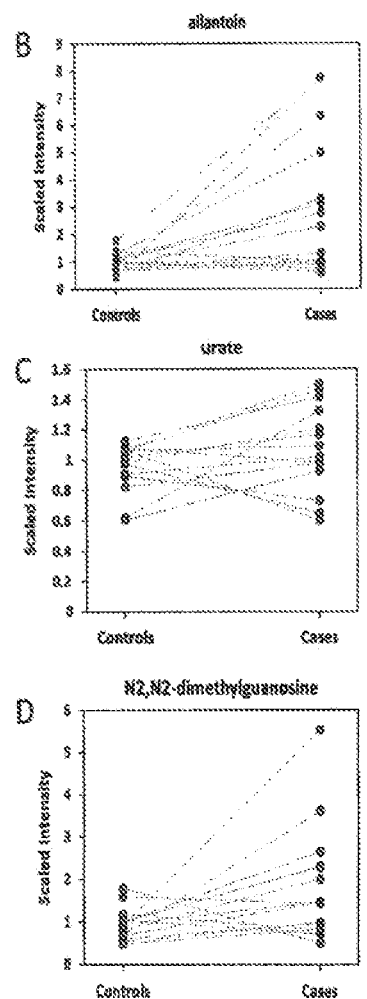
Figure 4:
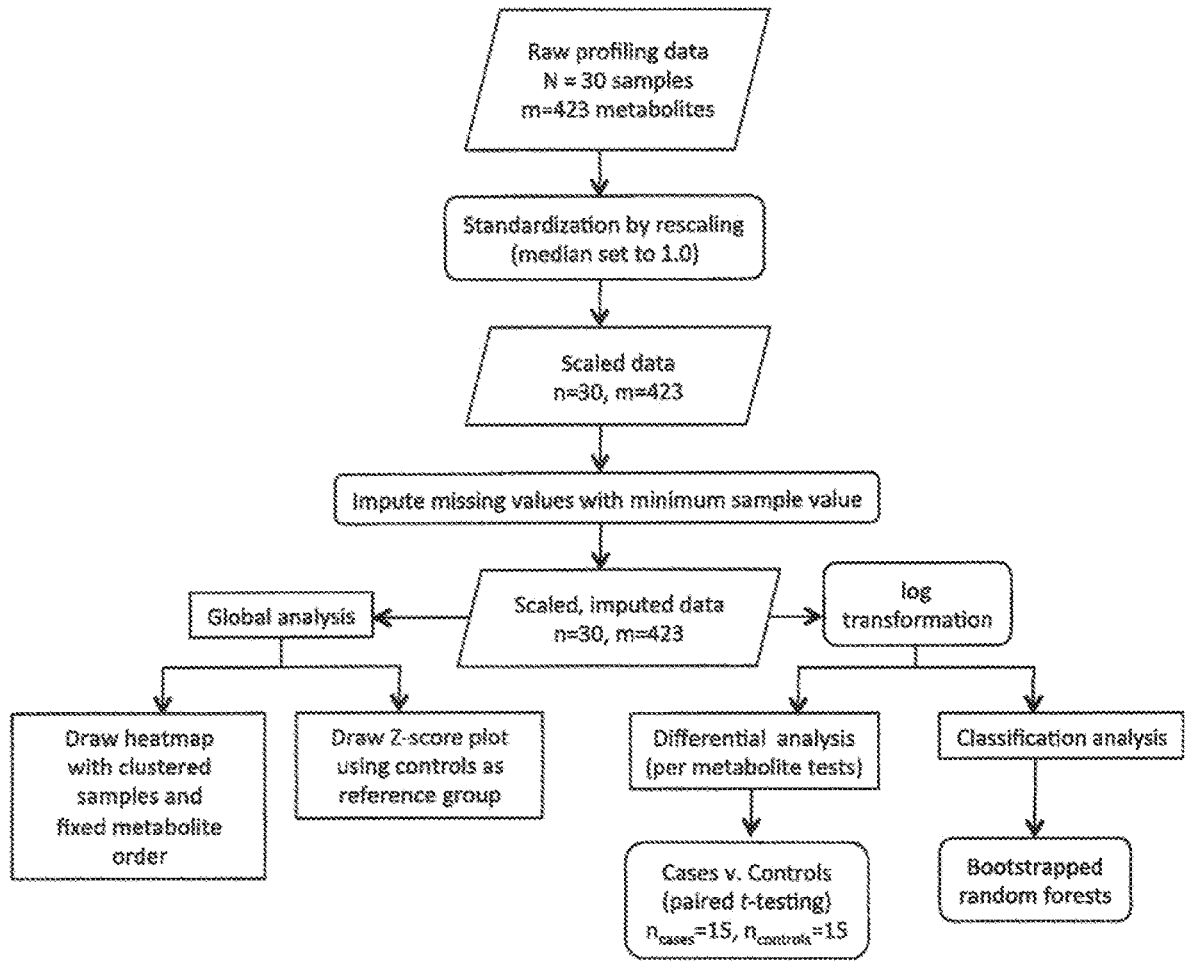
FIG. 4 demonstrates one embodiment a metabolomic profile analysis. Total N refers to sample size of patients, m refers to metabolites.

Evidence of oxidative stress was also found in purine metabolic pathways. For example, while similar levels of xanthine and urate (p=0.68, 0.36 respectively) were found; allantoin, a compound produced by free radical oxidation of uric acid (p<0.01), was increased in patient plasma. Modified purine nucleotides, also liberated during oxidative stress, were also elevated in patient plasma as compared to controls ($N_2$, $N_2$-dimethylguanosine (p<0.01), N6-carbamoylthreonyladenosine (p<0.05), and N1-methyladenosine (p<0.01)). See, FIG. 3.

IV. Metabolite-Based Classification Models

Plasma metabolites having significant differences between patients and controls were used to build prognostic models for death at 90 days among patients with pneumonia and sepsis at presentation. For example, random forest models demonstrated both sensitivity and specificity. See, Table 4.

TABLE 4

Performance of the classification models, including supervised random forest, (model 1) classification and regression trees (model 2), and XYZ (model 3).

| Class prediction model | Model Performance | | |
|---|---|---|---|
| | AUC | Sensitivity (%) | Specificity (%) |
| Model 1: Random forest analysis model characteristics | 0.67 (0.49, 0.84) | 0.67 (0.38, 0.88) | 0.67 (0.38, 0.88) |

In sensitivity analyses, the model performance was unchanged when the random forest seed was varied while using sparse PLS.

V. Cell Culture Experiments of Putative DAMPs

Biomarker metabolite profiles were validated by stimulating cytokine production in differentiated Thp1 monocytes in vitro in mouse liver and kidney homogenates at 8 h in cecal ligation and puncture (CLP) sepsis. For example, five nucleic acid metabolites were greater in non-survivors (p<0.05). Of these, pseudouridine (See, Table 2) increased monocyte expression of TNFα and IL1β versus control (p<0.05). Pseudouridine was also increased in liver and kidney homogenates from CLP mice versus sham (p<0.05 for both).

A. Monocyte Stimulation by Nucleic Acid Metabolites

To validate the biomarker metabolites in the metabolomic patterns, it was determined whether specific identified nucleic acid metabolites that were increased in non-survivors, could stimulate inflammatory cytokine responses in monocytes in vitro. See, Table 2.

Figure 5:
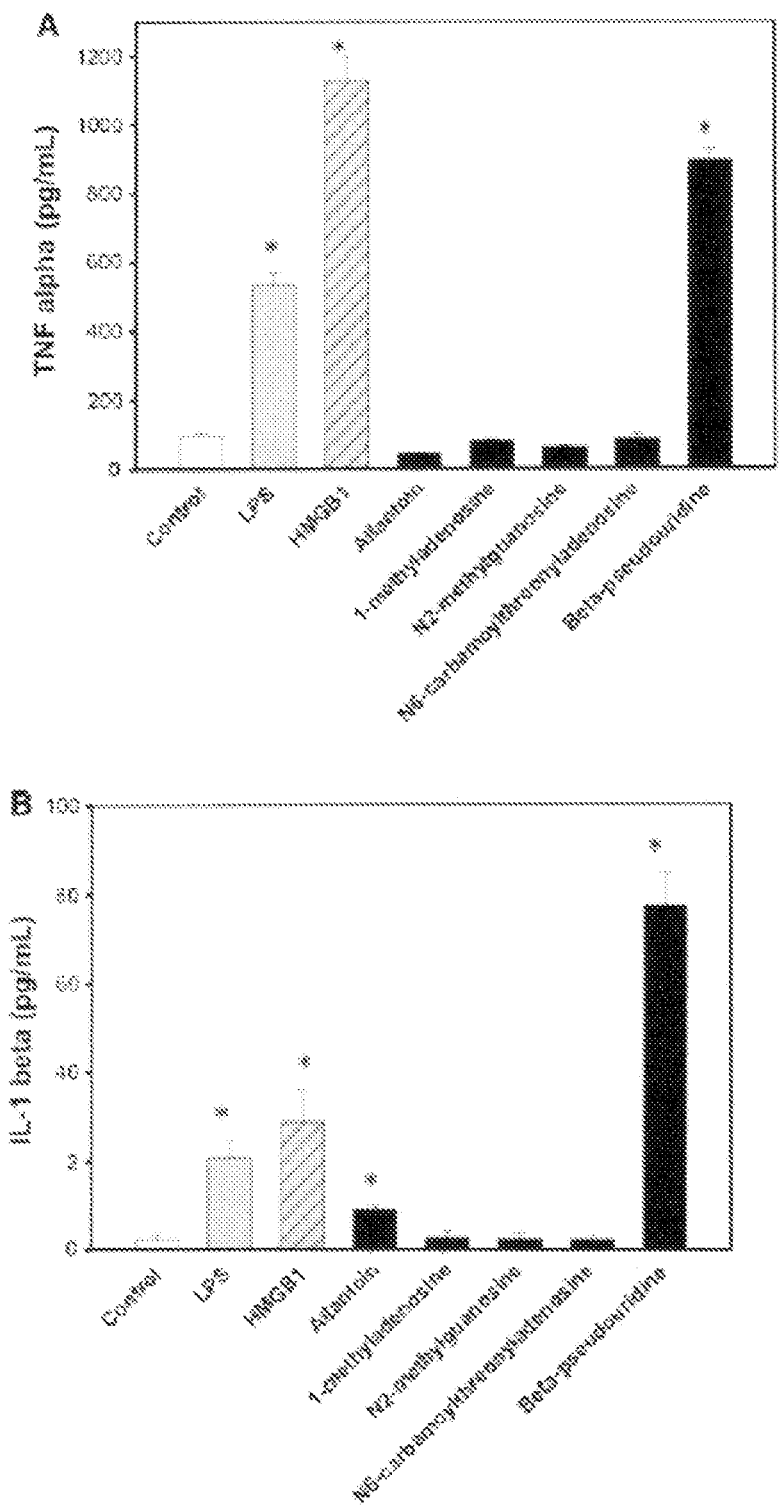
FIG. 5 presents exemplary data showing biomarker metabolites that stimulate monocytes/macrophages to induce cytokine production. Data represent mean±SEM. *p\0.05 vs. control; #p\0.05 vs. alone. Data representative of three separate experiments performed in duplicate or triplicate
Figure 5:
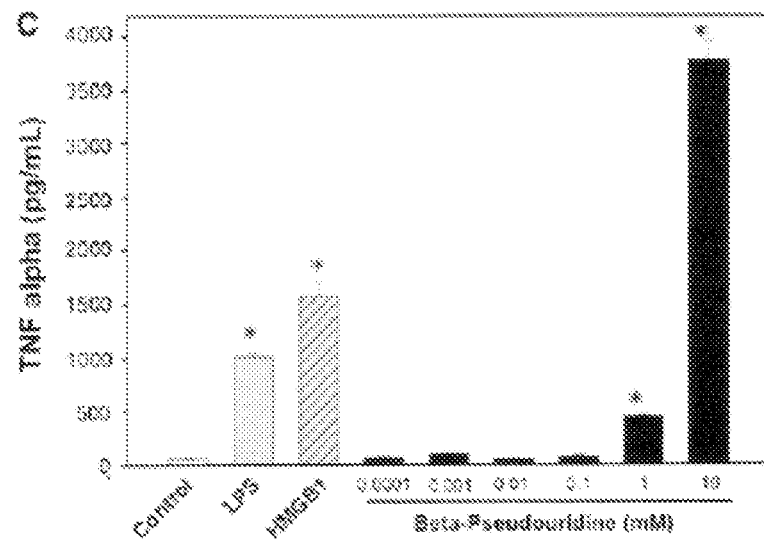
Figure 5:
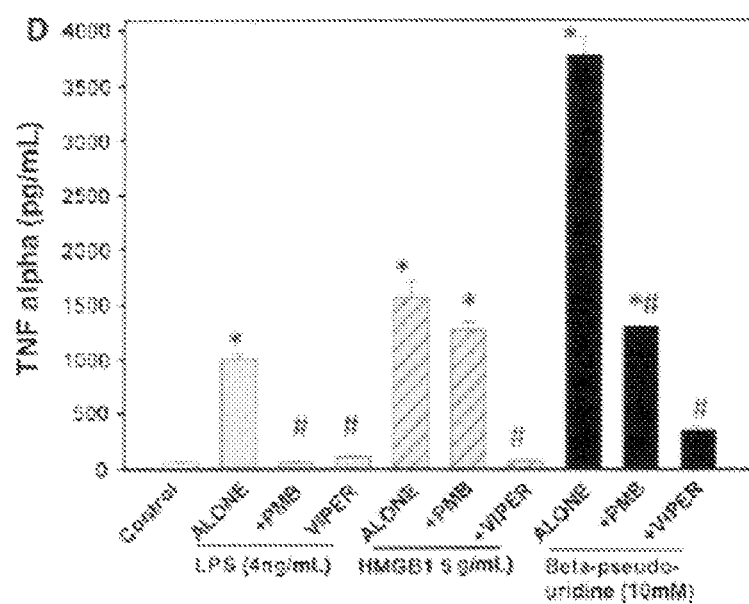

Differentiated Thp-1 human monocytes were treated for 16 h with betapseudouridine, 1-methyladenosine, N-2-methylguanosine, N-6-carbamoylthreonlyadenosine, or allantoin and compared TNFα and IL-1β levels in cell culture supernatants with levels in supernatants from cells treated with PBS only (control), a known DAMP (i.e., for example, HMGB-1) or LPS. The data demonstrated that beta-pseudouridine, a pyrimidine nucleotide, stimulated significant release of TNFα and IL-1β in supernatants, and allantoin also significantly increased IL-1β production but at lower levels. See, FIGS. 5A and 5B; p<0.05. Cytokine stimulation by beta-pseudouridine was concentration-dependent and greatest at higher metabolite concentrations. See, FIG. 5C. Cytokine levels remained significantly elevated in the presence of endotoxin-binding agent, polymyxin B, but were significantly abrogated in the presence of TLR4-receptor inhibitor (TLR4 inhibition by viral inhibitory peptide VIPER). See, FIG. 5D.

B. Cecal Ligation and Puncture Mouse Model

We observed a significant relative difference in both liver and kidney homogenate at 8 h after CLP compared to sham in pseudouridine (p<0.05, q<0.05 for both). Although N1-methyladenosine was significant greater in liver homogenate, it was not significantly different in kidney. No other differences were consistent across both liver and kidney compartments among candidate metabolites (e.g., N-2-methylguanosine, N-6-carbamoylthreonlyadenosine, or allantoin).

EXPERIMENTAL

Example I

Study Design, Patients, and Setting

An outcome-dependent, stratified random sample of subjects was drawn from the Genetic and Inflammatory Markers of Sepsis (GenIMS) cohort study. Breslow et al., "Maximum likelihood estimation of logistic regression parameters under two phase, outcome-dependent sampling" *J R Stat Soc Ser C Appl Stat* 1997; 59:447-461. GenIMS enrolled 1,895 subjects in the emergency departments of 28 hospitals in southwestern Pennsylvania, Connecticut, southern Michigan, and western Tennessee between November 2001 and November 2003. Kellum et al., "Understanding the inflammatory cytokine response in pneumonia and sepsis: results of the Genetic and Inflammatory Markers of Sepsis (GenIMS) Study" *Arch Intern Med* 2007; 167(15):1655-1663.

Subjects were greater than 18 years old and presented with a clinical diagnosis of pneumonia and a new pulmonary infiltrate on chest radiograph. Subjects were excluded if a) were transferred from another acute or chronic care hospital; b) discharged from an acute care hospital within the prior 10 days; c) incurred an episode of pneumonia within the past 30 days; d) had chronic mechanical ventilation dependency, cystic fibrosis, or active pulmonary tuberculosis; e) were admitted for palliative care; f) previously enrolled; or g) incarcerated or pregnant. Informed consent was obtained from the patient or a proxy, and the study was approved by the Institutional Review Boards of the University of Pittsburgh and all participating sites. Of the 2,320 subjects enrolled, 2,032 were admitted to hospital, and 137 were subsequently excluded because CAP was ruled out. Thus, the final inpatient sample was 1,895.

A subset of hospitalized patients was randomly selected and stratified by survival at 90 days. Then fifteen (15) patients that had died were matched with fifteen (15) control survivors on the following characteristics: 1) age (within 5 years), 2) sex (male), 3) race (white), 4) initial procalcitonin >0.25 mg/ml, 5) CAP organism gram stain (positive, negative, or unknown), 6) blood sample obtained at the time of presentation, and 7) no prior freeze/thaw cycle on blood sample.

Example II

Study Procedures and Blood Sampling

Among enrolled subjects, detailed baseline and clinical information was recorded from the subject or proxy, bedside assessments by research nurses, or the medical record. The clinical data were stripped of identifying information and merged with blood sample data. All data collection procedures were conducted under strict confidentiality and were audited and reviewed for accuracy. Blood samples in this study were drawn immediately following enrollment into pyrogen-free tubes containing heparin or citrate, and plasma separated by centrifugation into 1.5 mL tubes. Samples were immediately centrifuged and were stored frozen at −80° C. until assayed. Samples were shipped on dry ice to Metabolon, Inc., Durham, N.C. for further analysis.

Example III

Metabolomic Profiling

Metabolomic profiling was performed using a previously described platform. Lawton et al., "Analysis of the adult human plasma metabolome" *Pharmacogenomics* 2008; 9(4):383-397. Metabolites were identified using a mass spectrometry (MS)-based approach that included the following steps: 1) sample extraction and preparation, 2) detection, 3) spectral analysis, 4) normalization and imputation of missing values, 5) visualization of normalized data, and 5) delineation of class-specific metabolomics signatures.

In brief, all samples were accessioned into the Metabolon LIMS system and prepared by methanol extraction to remove protein fractions. The resulting extract was divided into fractions for subsequent UHPLC/MS/MS$^2$ (positive and negative modes) and GS/MS analysis. Following the appropriate sample preparation techniques, aliquots were separated for UHPLC/MS/MS$^2$ analysis using a Waters Acquity UPLC and analyzed using an LTQ mass spectrometer. Derivatized samples were separated for GC/MS on a 5% phenyl dimethyl silicone column with helium as the carrier gas, and analyzed samples on a Thermo-Finnigan Trace DSQ mass spectrometer.

Metabolites were identified by automated comparison of the ion features of the experimental samples to a reference library of chemical standard entries that included retention time, molecular weight (m/z), preferred adducts, and in-source fragments as well as associated MS spectra. They were curated by visual inspection for quality control using software developed at Metabolon. Dehaven et al., "Organization of GC/MS and LC/MS metabolomics data into chemical libraries" *J Cheminform* 2010; 2(1):9. To assist with data visualization, raw area counts were resealed for each metabolite by dividing all sample values by the median value for each individual metabolite. For statistical analyses, any missing values were assumed to be below the limits of detection and these values were imputed with the compound minimum (minimum value imputation).

To visualize how metabolite expressions deviated from controls, a z-score analysis was used to scale each metabolite according to the mean and standard deviation of the control samples. Per metabolite, cases were centered by the control mean and scaled by the control standard deviation. Metabolomic patterns were also visualized using heat maps generated from unsupervised clustering of samples within each group (patients or controls) with a fixed metabolite order. Data was median centered, per metabolite, and a green/red color scheme was used to indicate an increase or decrease in a metabolite, respectively, relative to the median metabolite level across all samples.

Example IV

Other Cytokine Assays

Interleukin (IL)-6, IL-10, and tumor necrosis factor was measured using an automated immunoassay analyzer (IM-MULITE System, Diagnostic Products, Los Angeles, Calif.). Upper limits of the normal range for each cytokine was based on the manufacturer's specifications for each assay: IL-6, 5.9 pg/mL; IL-10, 9.1 pg/mL; and tumor necrosis factor, 8.1 pg/mL. All laboratory personnel were blinded to clinical information.

Example V

Statistical Analysis

All statistical analyses were performed using STATA 11.0 (College Station, Tex.) or the program R (cran.r-project.org). The Wilcoxon signed rank test and paired, Student's t-test were used to evaluate if baseline and pre-infection characteristics were similar across matched pairs. To compare cases and controls for levels of metabolites, the relative observed concentrations for each metabolite was log transformed, and used two-sided paired Welch's t-tests identifying statistical significance at p=0.05. False discovery rates (FDR) were estimated for each biochemical using q values to account for multiple comparisons. Storey et al., "Statistical significance for genomewide studies" *Proceedings of the National Academy of Sciences of the United States of America* 2003; 100(16):9440-9445. Only metabolites with q<0.1 were selected for illustration.

Example VI

Metabolic Profiling

The non-targeted metabolic profiling techniques employed for this analysis combined three independent platforms as described previously. Ohta et al., "Untargeted metabolomic profiling as an evaluative tool of fenofibrate-induced toxicology in Fischer 344 male rats" *Toxicol. Pathol.* 2009; 37(4)521: and Evans et al., "Integrated, non-targeted ultrahigh performance liquid chromatography/electrospray ionization tandem mass spectrometry platform for the identification and relative quantification of the small-molecule complement of biological systems" *Anal. Chem.* 2009; 81:6656-67.

Sample Accessioning and Preparation:

Each sample received was accessioned into the Metabolon LIMS system, assigned a unique identifier associated with only the original source identifier, and stored at −80° C. until processing. The LIMS identifier was used to track all sample handling, tasks, results, etc. The samples (and all derived aliquots) were tracked by the LIMS system. All portions of any sample were automatically assigned their own unique identifiers by the LIMS system when a new task was created; the relationship of these samples was also tracked.

Samples were prepared using the automated MicroLab STAR® robotics system (Hamilton Company, Salt Lake City, Utah). 1000 of each sample was used for analyses. To remove protein, dissociate small molecules bound to protein or trapped in the precipitated protein matrix, and to recover chemically diverse metabolites, proteins were precipitated with aqueous methanol with vigorous shaking for 2 minutes.

Methanol used for extraction contained 4 standards to report on extraction efficiency for QC purposes.

Samples were then centrifuged, supernatant removed, and split into four equal volumes for analysis by UHPLC/MS/MS2 (positive mode), UHPLC/MS/MS2 (negative mode), GC/MS, and one aliquot was retained as a reserve. Samples were placed briefly on a TurboVap® (Zymark, Hopkinton, Mass.) to remove the organic solvent and dried under vacuum. Samples were then reconstituted in 50 μl 0.1% formic acid in water (positive conditions) or in 50 μl 6.5 mM ammonium bicarbonate in water, pH 8 (negative conditions) for the two UHPLC/MS/MS2 analyses. The LC-compatible solvents used for reconstitution of samples contained 8 or more injection standards at fixed concentrations (to ensure both injection and chromatographic consistency).

For GC/MS analysis, samples were derivatized to a final volume of 50 μl using equal parts bistrimethyl-silyl-trifluoroacetamide and solvent mixture acetonitrile:dichloromethane:cyclohexane (5:4:1) with 5% triethylamine at 60° C. for 1 hour. The derivatization mixture also contained a series of alkyl benzenes for use as retention time markers.

Example VII

Ultrahigh Performance Liquid Chromatography/Tandem Mass Spectrometry (LC/MS/MS2) and Gas Chromatography/Mass Spectrometry (GC/MS)

The LC/MS portion of the platform incorporates a Waters Acquity UPLC system (Waters, Millford, Mass.) and a Thermo-Finnigan LTQ mass spectrometer (Thermo Fisher Scientific, Inc., Waltham, Mass.), including an electrospray ionization (ESI) source and linear ion-trap (LIT) mass analyzer. The MS instrument scanned 99-1000 m/z and alternated between MS and MS2 scans using dynamic exclusion with approximately 6 scans per second. For the positive ion and negative ion optimized conditions, two independent injections using separate dedicated columns were performed. Extracts were loaded onto columns (Waters UPLC BEH C18-2.1×100 mm, 1.7 μm) and gradient-eluted with water and 95% methanol containing 0.1% formic acid (acidic extracts) or 6.5 mM ammonium bicarbonate (basic extracts). For the GC/MS portion of the platform, derivatized samples were separated on a 5% phenyl dimethyl silicone column with helium as the carrier gas and a temperature ramp from 60° C. to 340° C. over a 17 minute period. All samples were then analyzed on a Thermo-Finnigan Trace DSQ fast-scanning single-quadrupole mass spectrometer (Thermo Fisher Scientific, Inc., Waltham, Mass.) operated at unit mass resolving power with electron impact ionization and a 50-750 atomic mass unit scan range. The instrument was tuned and calibrated for mass resolution and mass accuracy on a daily basis.

Example VIII

Quality Assurance/Control

All columns and reagents were purchased in bulk from a single lot to complete all related experiments. For monitoring of data quality and process variation, multiple replicates of a pool of well-characterized human plasma were injected throughout the run, interspersed among the experimental samples, in order to serve as technical replicates for calculation of precision. In addition, process blanks and other quality control samples were spaced evenly among the injections, and all experimental samples were randomly distributed throughout the run. As mentioned previously, a selection of QC compounds carefully chosen so as to not interfere with the measurement of endogenous compounds was added to every sample for chromatographic alignment.

Example IX

Bioinformatics

The Metabolon LIMS system encompasses sample accessioning, preparation, instrument analysis and reporting, and advanced data analysis. Additional informatics components include data extraction into a relational database and peak-identification software, proprietary data processing tools for QC and compound identification, and a collection of interpretation and visualization tools for use by data analysts. The hardware and software systems are built on a web-service platform utilizing Microsoft's .NET technologies which run on high-performance application servers and fiber-channel storage arrays in clusters to provide active failover and load-balancing.

Example X

Biomarker Metabolite Identification, Quantification, and Data Curation

Biomarker metabolites were identified by automated comparison of the ion features generated from the experimental samples to a reference library of purified, authentic chemical standard entries that included retention time, molecular weight (m/z), preferred adducts, and in-source fragments as well as associated MS spectra. At present more than 2500 commercially-available purified standards are registered into LIMS for distribution to both the LC and GC platforms for determination of their analytical characteristics.

Chromatographic properties and mass spectra allow matching to a specific compound or an isobaric entity using proprietary visualization and interpretation software. Additional recurring entities may be identified as needed via acquisition of a matching purified standard or by classical structural analysis. Peaks were quantified using area-under-the-curve. Subsequent QC and curation processes were designed to ensure accurate, consistent identification, and to minimize system artifacts, mis-assignments, and background noise. Curation of all data was carried out by visual inspection for QC using software developed at Metabolon.

Example XI

Data Normalization, Imputation, and Statistical Analysis

To assist with data visualization, raw area counts for each biomarker metabolite were resealed by dividing all sample values by the median value for each individual metabolite. This correctly preserves all variation between samples, yet allows metabolites of widely different raw peak areas to be compared directly on a similar graphical scale. Each individual determination was then expressed as a ratio relative to this median value, to determine fold-changes in metabolite concentrations.

For statistical analysis and data display purposes, missing values (if any) were assumed to be below the level of detection and these values were imputed with the compound minimum (minimum value imputation). Statistical analysis of metabolomics data was performed using "R" (cran.r-project.org/), which is a freely available, open-source software package. Log transformation was applied to the relative observed concentrations for each metabolite prior to statistical analysis to produce a more normal distribution of the data. Between-group relative differences were assessed using two-sided, paired Welch's t-tests and statistical significance was assumed at p=0.05. Multiple comparisons were accounted for by estimating false discovery rates (FDR) for each biochemical using q-values. Only metabolites with q<0.1 were selected for illustration purposes.

Example XII

In-Vitro Monocyte Stimulation

Among significant metabolites (p<0.05, q<0.1) in our agnostic approach, five nucleic acid metabolites (e.g., beta-pseudouridine, 1-methyladenosine, N-2-methylguanosine, N-6-carbamoylthreonyladenosine, and allantoin) were identified for in vitro monocyte stimulation experiments. See, Table 2. These nucleic acid metabolites may function as damage-associated molecular patterns, and stimulate TNFα and IL1β similar to HMGB-1 and LPS. Bleiblo et al. (2012) "The role of immunostimulatory nucleic acids in septic shock" *Int J Clin Exp Med* 5:1-23

THP-1 cells (American Type Cell Collection, Manassas, Va., USA) were cultured in suspension in RPMI1640 media (Gibco, Grand Island, N.Y., USA) supplemented with 10% fetal bovine serum, 2 mM L-glutamine, 100 U/mL penicillin, 100 U/mL streptomycin, and 100 lM sodium pyruvate (all from Gibco). To differentiate the monocytes, $0.33 \times 10^6$ cells/mL were suspended in media and treated with 5 ng/mL PMA and then plated. After 48 h, adhered cells were washed three times in PBS and then treated for 16 h with compounds of interest at concentrations described. All compounds were dissolved in endotoxin-free water.

Endotoxin was measured at 61.5-153.8 pg per 250 lL treatment of 10 mM dose beta-pseudouridine, compared to 4,000 pg/mL in LPS-positive control. After 16 h media was collected and TNFα and IL1β levels determined by ELISA (R&D Systems, Minneapolis, Minn., USA) according to manufacturer's instructions. Experiments were repeated after treatment with viral inhibitory peptide of TLR4 (VIPER) and polymyxin B (PMB).

Example XIII

Cecal Ligation and Puncture Sepsis Model

Animal protocols were approved by the University of Pittsburgh Institution Animal Care and Use Committee. The experiments were performed in adherence to the National Institutes of Health Guidelines on the use of laboratory animals.

Cecal ligation and perforation (CLP) was performed on C57BL/6 male mice (Jackson Laboratories, Bar Harbor, Me., USA) aged 6-8 weeks and weighing 20-25 g. These animals were anesthetized with pentobarbital (70 mg/kg IP). A 1- to 2-cm mid-line laparotomy was performed and the cecum identified.

Stool was then milked to the tip of the cecum and it was subsequently ligated 1 cm from the tip with a 2-0 silk tie. The cecum is then perforated with a 22G needle and returned into the abdomen. The muscular and skin was closed with a running 2-0 silk suture. Sham animals underwent laparotomy and bowel manipulation without ligation or perforation (also referred to in this text as sham CLP). Mice were sacrificed 8 h post-CLP, the circulation was flushed with cold PBS, and liver and kidney were harvested and snap frozen. No antibiotics were utilized and animals had free access to food and water pre- and post-operatively. Frozen liver and kidney were prepared for analysis using Metabolon's standard solvent extraction method. The extracted samples were split into equal parts for analysis on the GC/MS and LC/MS/MS platforms.

We claim:
1. A method comprising:
   a) providing;
      i) a biological sample derived from a patient suspected of having sepsis or pneumonia; and
      ii) a metabolomic platform capable of generating a heat map displaying a pattern comprising a plurality of low molecular weight biomarker metabolites, wherein said low molecular weight biomarker metabolites are selected from the group consisting of N-acetyl serine, glycocholenate sulfate, taurochenolate sulfate, 2-oleoylglycerophosphoethanolamine, 1-linoleoylglycero-phosphoethanolamine, alpha-CEHC glucuronide, N1-methyl-2-pyridone-5-carboxamide, S-methylcysteine, N-acetylphenylalanine, 2-linoleoylglycerophosphoethanolamine and 1-arachidonoylglycerophosphoethanolamine; and
   b) contacting said sample with said platform under conditions that displays said heat map of said plurality of low molecular weight biomarker metabolites;
   c) identifying said patient with a higher risk for sepsis or pneumonia with a prognosis of not surviving for at least 90 days based on said pattern of plurality of low molecular weight biomarker metabolites as compared to the risk of a control subject for sepsis or pneumonia with an at least 90 day survival prognosis; and
   d) treating said higher risk patient with an early therapy such that said higher risk patient survives, wherein said early therapy is selected from the group consisting of antibiotics, corticosteroids, mechanical ventilation and nutritional supplements.

2. The method of claim 1, wherein said higher risk for sepsis or pneumonia is identified by the relative abundance of said plurality of low molecular weight biomarker metabolites of said biomarker metabolite pattern.

3. The method of claim 1, wherein said plurality of low molecular weight biomarker metabolites is selected from the group consisting of at least one hundred (100) biomarker metabolites, at least two hundred (200) biomarker metabolites, at least three hundred (300) biomarker metabolites, and at least four hundred (400) biomarker metabolites.

4. The method of claim 3, wherein said plurality of biomarker metabolites comprises bile acid biomarker metabolites.

5. The method of claim 3, wherein said plurality of biomarker metabolites comprises oxidative stress biomarker metabolites.

6. The method of claim 1, wherein said pattern comprises a damage-associated molecular pattern.

7. The method of claim 1, wherein said heat map further comprises a plurality of biomarker metabolite regions.

8. The method of claim 7, wherein said plurality of biomarker metabolite regions are selected from the group consisting of an amino acid biomarker region, a peptide region, a carbohydrate region, an energy biomarker region, a lipid biomarker region, a nucleotide biomarker region, a cofactor/vitamin biomarker region and a xenobiotic biomarker region.

9. A metabolomic platform comprising a heat map display, said heat map display comprising a patient metabolomic sepsis or pneumonia profile, wherein said metabolomic profile comprises a plurality of low molecular weight biomarker metabolites selected from the group consisting of N-acetyl serine, glycocholenate sulfate, taurochenolate sulfate, 2-oleoylglycerophosphoethanolamine, 1-linoleoyl-glycero-phosphoethanolamine, alpha-CEHC glucuronide, N1-methyl-2-pyridone-5-carboxamide, S-methylcysteine, N-acetylphenylalanine, 2-linoleoylglycerophospho-ethanolamine and 1-arachidonoylglycerophosphoethanolamine that provides for a prognosis that said patient survives for at least ninety (90) days.

10. The metabolomic platform of claim 9, wherein said heat map further comprises a plurality of biomarker metabolite regions are selected from the group consisting of an amino acid biomarker region, a peptide region, a carbohydrate region, an energy biomarker region, a lipid biomarker region, a nucleotide biomarker region, a cofactor/vitamin biomarker region and a xenobiotic biomarker region.

11. The metabolomic platform of claim 10, wherein said amino acid biomarker region comprises a biomarker metabolite selected from the group consisting of an increased N-acetyl serine biomarker, an increased C-glycosyltryptophan biomarker, an increased kynurante biomarker, and an increased urea biomarker as compared to a normative population.

12. The metabolomic platform of claim 10, wherein said carbohydrate biomarker region comprises a biomarker metabolite selected from the group consisting of an increased erythonate biomarker, an increased mannitol biomarker, an increased glycerate biomarker, and an increased xylonate biomarker as compared to a normative population.

13. The metabolomic platform of claim 10, wherein said energy biomarker region comprises an increased fumarate biomarker as compared to a normative population.

14. The metabolomic platform of claim 10, wherein said lipid biomarker region comprises a biomarker metabolite selected from the group consisting of an increased glycocholenate sulfate biomarker, an increased taurochenolate sulfate biomarker, an increased 10-heptadecenoate (17:1n7) biomarker, an increased 2-oleoylglycerophospho-ethanolamine biomarker, an increased 1-linoleoylglycero-phosphoethanolamine biomarker and an increased cortisol biomarker as compared to a normative population.

15. The metabolomic platform of claim 10, wherein said nucleotide biomarker region comprises a biomarker metabolite selected from the group consisting of increased N1-methyladenosine biomarker, and an increased pseudouridine biomarker as compared to a normative population.

16. The metabolomic platform of claim 10, wherein said cofactor/vitamin region comprises a biomarker metabolite selected from the group consisting of an increased alpha-CEHC glucuronide biomarker, an increased pyridoxate biomarker, and an increased N1-methyl-2-pyridone-5-carboxamide biomarker as compared to a normative population.

17. The metabolomic platform of claim 10, wherein said xeobiotic biomarker region comprises a biomarker metabolite selected from the group consisting of an increased paraxanthine biomarker, an increased caffeine biomarker, and an increased erythitol biomarker as compared to a normative population.

18. A metabolomic platform comprising a heat map display, said heat map display comprising a metabolomic profile, wherein said metabolic profile comprises a plurality of biomarker metabolite regions derived from a patient diagnosed with sepsis or pneumonia, wherein at least one of said plurality of biomarker metabolite regions comprises a bile acid biomarker region wherein said bile acid region comprises a biomarker selected from the group consisting of glycocholenate sulfate and taurochenolate sulfate.

* * * * *